United States Patent
Pohlman et al.

(10) Patent No.: US 8,502,662 B2
(45) Date of Patent: Aug. 6, 2013

(54) METHOD AND SYSTEM FOR USING STATUS INDICATORS IN WIRELESS COMMUNICATION WITH MEDICAL DEVICES

(75) Inventors: David Pohlman, Malvern, PA (US); Krzysztof Brukalo, Chambersburg, PA (US)

(73) Assignee: Animas Corporation, West Chester, PA (US)

( * ) Notice: Subject to any disclaimer, the term of this patent is extended or adjusted under 35 U.S.C. 154(b) by 458 days.

(21) Appl. No.: 12/494,575

(22) Filed: Jun. 30, 2009

(65) Prior Publication Data

US 2009/0326722 A1 Dec. 31, 2009

Related U.S. Application Data

(60) Provisional application No. 61/076,823, filed on Jun. 30, 2008.

(51) Int. Cl.
*G08B 21/00* (2006.01)

(52) U.S. Cl.
USPC .......... 340/540; 340/539.12; 604/65; 607/60; 715/771

(58) Field of Classification Search
USPC ..... 340/539.1, 539.12, 540; 128/903; 604/65; 607/60; 700/282; 715/771, 772; 370/278
See application file for complete search history.

(56) References Cited

U.S. PATENT DOCUMENTS

| | | | |
|---|---|---|---|
| 5,285,450 A | | 2/1994 | Emerson |
| 6,554,798 B1 | | 4/2003 | Mann et al. |
| 6,974,437 B2 | | 12/2005 | Lebel et al. |
| 7,764,673 B1 | | 7/2010 | Asawa et al. |
| 7,778,285 B2 | | 8/2010 | Bleisteiner et al. |
| 7,811,231 B2 | | 10/2010 | Jin et al. |
| 8,121,060 B2 | | 2/2012 | Kwa et al. |
| 2002/0016568 A1* | | 2/2002 | Lebel et al. .......... 604/131 |
| 2004/0068230 A1 | | 4/2004 | Estes et al. |
| 2005/0022274 A1 | | 1/2005 | Campbell et al. |
| 2005/0215982 A1 | | 9/2005 | Malave et al. |
| 2007/0093786 A1 | | 4/2007 | Goldsmith et al. |
| 2008/0033357 A1 | | 2/2008 | Mann et al. |
| 2009/0326722 A1 | | 12/2009 | Pohlman et al. |
| 2010/0313115 A1 | | 12/2010 | Varone et al. |
| 2011/0191632 A1 | | 8/2011 | Miller |

FOREIGN PATENT DOCUMENTS

| | | |
|---|---|---|
| EP | 1338295 A1 | 8/2003 |
| EP | 1839694 A1 | 10/2007 |
| EP | 2009533 A1 | 12/2008 |
| EP | 2062527 A1 | 5/2009 |

OTHER PUBLICATIONS

European Search Report dated Apr. 11, 2009, EP Patent application No. 09251689.7.

* cited by examiner

*Primary Examiner* — Jeffery Hofsass

(57) ABSTRACT

The invention, in general, relates to communications systems for medical devices. In particular, the present invention is directed toward a communications routine for a medical infusion devices and a remote control unit that includes data elements within the transmissions that indicate the operating status of the infusion device.

4 Claims, 3 Drawing Sheets

METHOD AND SYSTEM FOR USING STATUS INDICATORS IN WIRELESS COMMUNICATION WITH MEDICAL DEVICES

FIELD OF THE INVENTION

The present invention relates, in general, to drug delivery systems and, more particularly, to a communications system for a drug delivery device that may be remotely controlled. The present invention also relates to methods and systems for communicating between a medical infusion device and a remote control and/or data acquisition unit.

BACKGROUND OF THE INVENTION

External infusion devices (e.g., infusion pumps) may be used for delivering medication to users, such as insulin to diabetics. Portable external infusion devices may be attached to a user's belt, for example, or placed in a user's pocket. In external infusion devices delivering insulin, for example, the insulin may delivered via a cannula, inserted in subcutaneous tissue of the user.

Some conventional external infusion pumps may communicate remotely with another controlling device, such as a remote controller that is physically separated from the external infusion pump, for altering one or more functional settings of the external infusion pump. One example of such device is shown and described in U.S. Pat. No. 6,554,798. Another example is shown and described in US Patent Application Publication Nos. 2005/0022274 and 2005/0215982. Other conventional infusion pumps may include a remote controller with a blood glucose measurement device. One example of such device is shown and described in US Patent Application Publication No. 2004/0068230.

Although these known devices are convenient to the diabetic users, applicants have discovered that there could be issues with the conventional infusion pumps that have not been recognized or identified in the art. For example, while an RF programmer (as in U.S. Pat. No. 6,554,798) could be programmed to learn a code unique to the infusion pump or to transmit a unique code to the infusion pump, there is nothing to confirm that: (a) the remote programmer is the one expressly designated to control (i.e., "paired") a specific infusion pump, and (b) the infusion pump is the one expressly designated as the device to be controlled (i.e., "paired") to a specified remote programmer. That is, in a scenario where several diabetes patients are closely intermingled with each other while configuring their respective pumps or meters (e.g., as in a pump training session), there is believed to be a greater likelihood that a first user may inadvertently couple the first user's remote programmer to a second or third user's pump, and the second or third user may couple the second or third user's remote programmer to the first user's pump. Such inappropriate control of the infusion pumps by the remote controller could be problematic for these users. Moreover, in another scenario of the RF programmer identified in the prior art, there is nothing to allow for easy and convenient recognition by the user that the pump selected to be paired with a specified remote controller is the correct pump. This could lead to a scenario where multiple pump users in a single household may inadvertently use each other's remote programmers or controlling each other's pumps. Where the remote controller includes a blood glucose measurement unit, inadvertent mix up between the remote controller and its assigned user may lead to issues with the infusion pump providing the wrong insulin doses.

Thus, applicants have recognized the potential risks in the known infusion pump and have developed various embodiments of a remote controller, medical device, systems, and methods that are believed to overcome or alleviate at least the above-identified drawbacks.

DETAILED DESCRIPTION OF ILLUSTRATIVE EMBODIMENTS OF THE INVENTION

Figure 1:
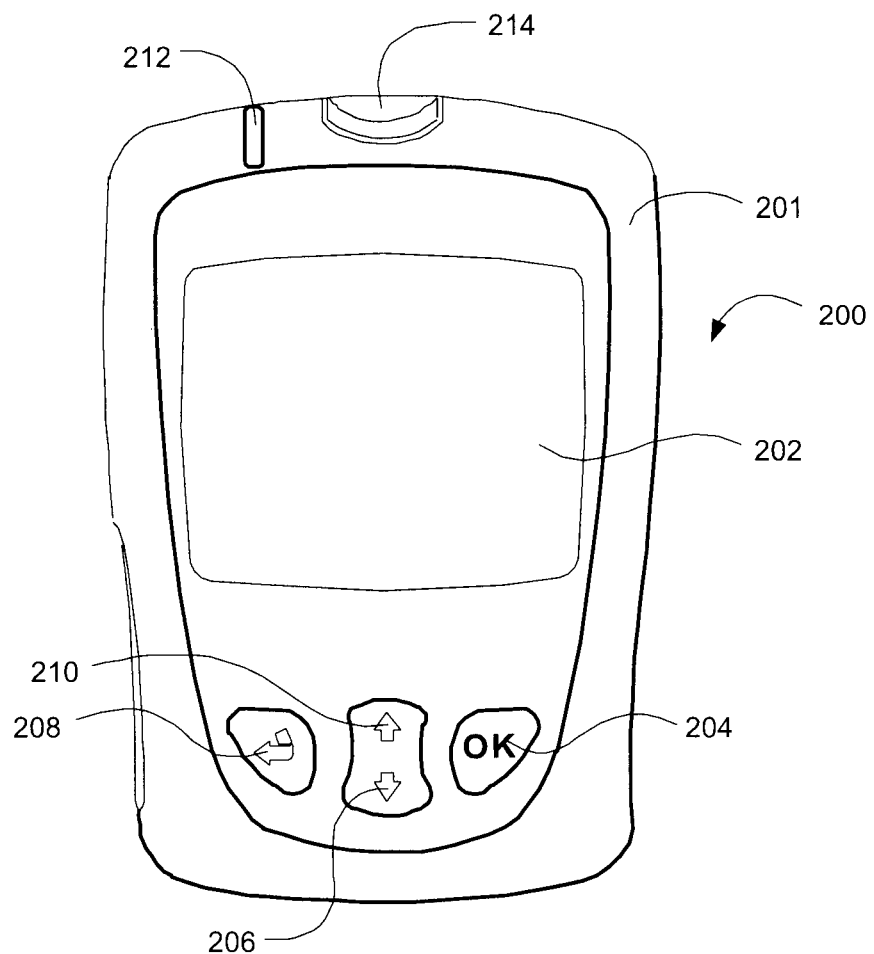
FIG. 1 is a plan view of a remote controller.

FIG. 1 is a plan view of a remote controller 200 that includes a first housing 201, a first display 202, an first OK button 204, a first down button 206, back button 208, a first up button 210, light emitting diode (LED) 212, and strip port connector (SPC) 214. Remote controller 200 can be configured to measure glucose episodically and communicate wirelessly with a medical device such as, for example, an insulin pump. In an embodiment, remote controller 200 can be similar to a commercially available glucose test meter such as, for example, OneTouch Ultra glucose meter from LifeScan Inc. (Milpitas, Calif.). In addition, the glucose meter can measure glucose episodically using a commercially available OneTouch Ultra test strip also from LifeScan Inc. (Milpitas, Calif.).

Figure 2:
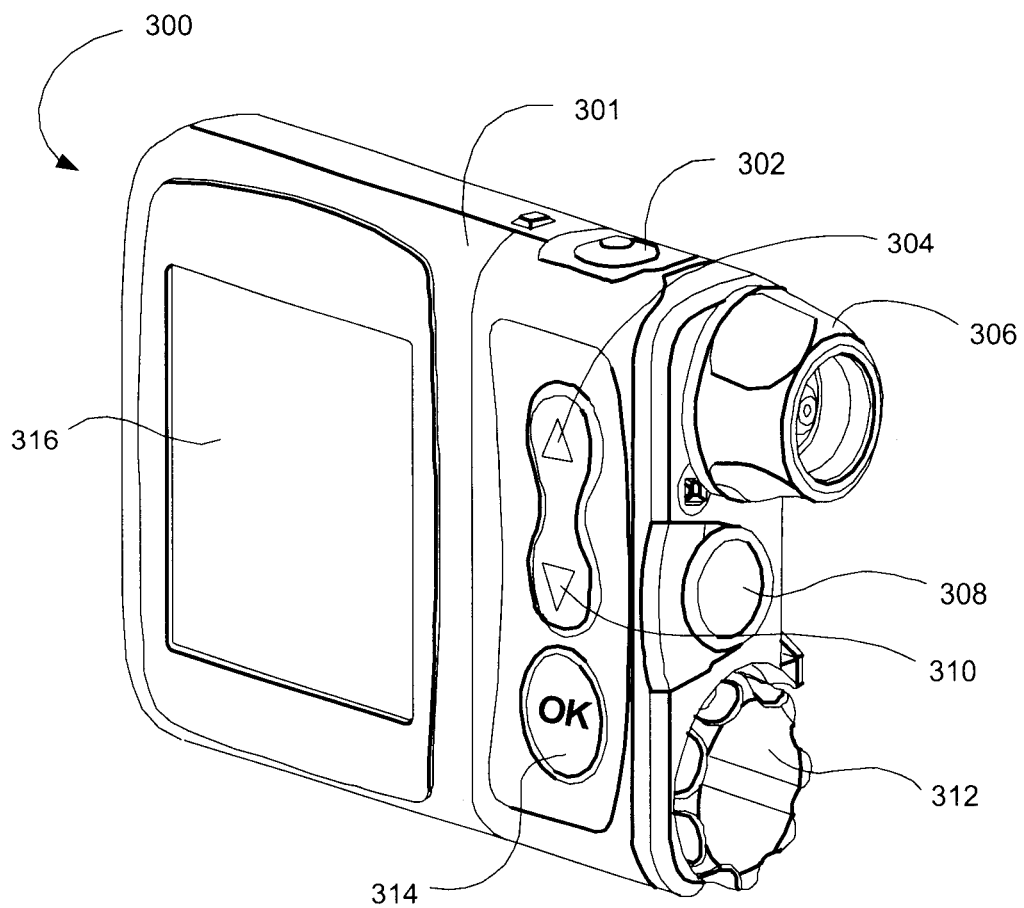
FIG. 2 is a perspective view of a pump.

FIG. 2 is a perspective view of a pump 300 that includes a second housing 301, a backlight button 302, a second up button 304, a cartridge cap 306, a bolus button 308, a second down button 310, a battery cap 312, a second OK button 314, and a second display 316. Pump 300 can be configured to dispense medication such as, for example, insulin for regulating glucose levels. Pump 300 can be similar to a commercially available pump from Animas, Corp. (West Chester, Pa., Catalog No. IR 1200).

Figure 3:
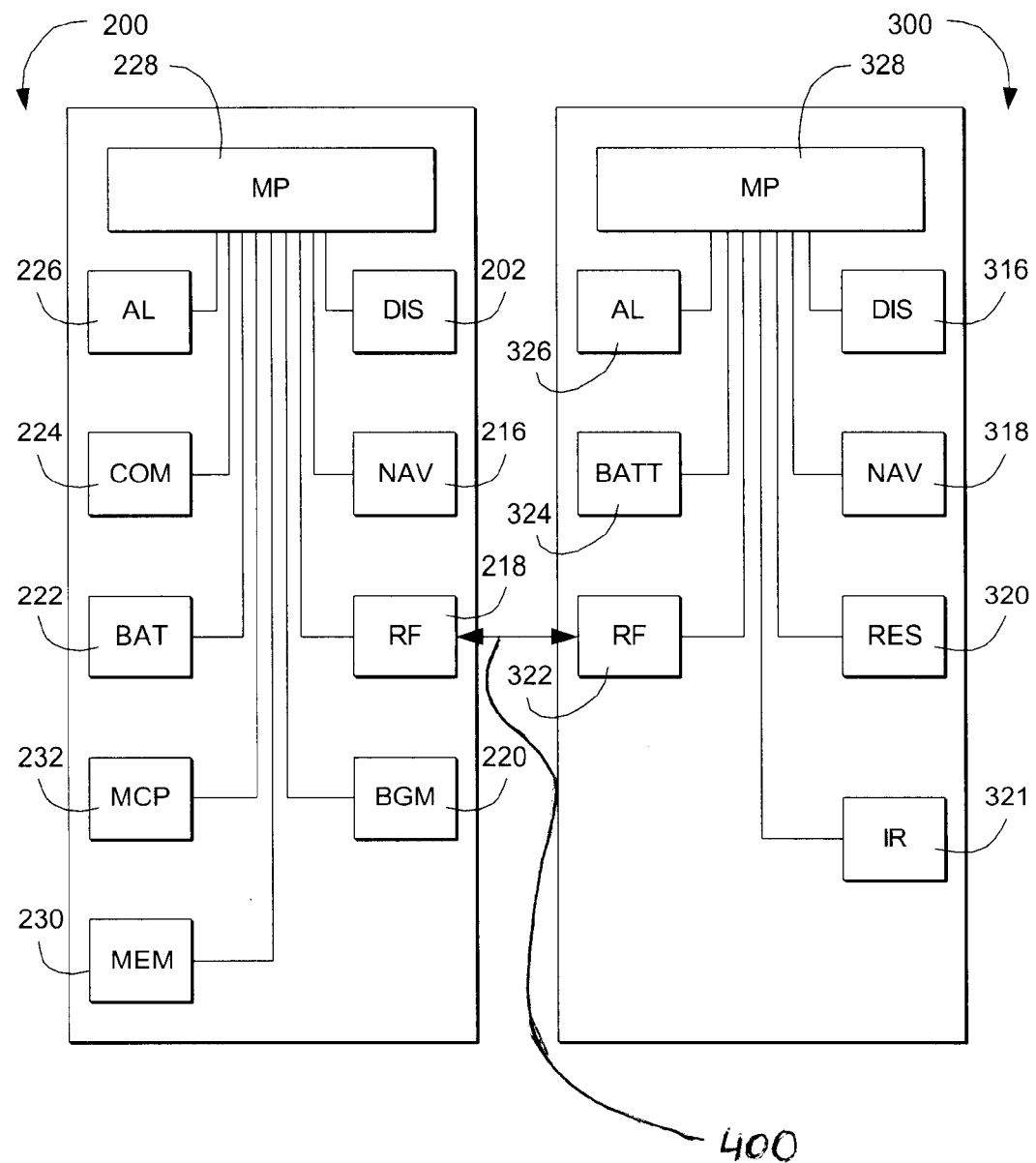
FIG. 3 is a schematic view of wireless communication between the remote controller and the pump.

FIG. 3 is a schematic functional view of remote controller 200 wirelessly communicating with pump 300. Remote controller 200 includes the following functional components that are a first display (DIS) 202, a first navigational buttons (NAV) 216, a first radio frequency module (RF) 218, a blood glucose measurement (BGM) module 220, a first battery (BAT) 222, a wired communication port (COM) 224, a first alarm (AL) 226, a first microprocessor (MP) 228, a memory portion (MEM) 230, and a memory chip port (MCP) 232. Pump 300 includes the following functional components that are a second display (DIS) 316, second navigational buttons (NAV) 318, a reservoir (RES) 320, an infrared communication port (IR) 321, a second radio frequency module (RF) 322, a second battery (BAT) 324, a second alarm (AL) 326, and a second microprocessor (MP) 328.

Pump 300 and remote controller 200 can bi-directionally communicate using a wireless signal 400 via first RF module 218 and second RF module 322. Remote controller 200 can send a command to pump 300 to perform a specific function such as to start or stop pumping insulin. More particularly, remote controller 200 can provide a basal pumping rate, a duration of time for pumping, a bolus amount, and a combination of a basal pumping rate and a bolus amount.

In an embodiment, remote controller 200 can be a master device and pump 300 can be a slave device. During use, there can be a need to determine the status of pump 300. For example, a user may need to know if pump 300 has a low reservoir of insulin, an occlusion, or a low battery power. To keep a user informed about the status of pump 300, remote controller 200 can actively interrogate pump 300 for status at a recurring time interval. When pump 300 receives a wireless request from remote controller 200, pump 300 can send a status message to remote controller 200. In an embodiment, remote controller 200 can interrogate pump 300 for status at a relatively high frequency so that a user can be notified immediately of any status changes. Although high frequency auto-polling is one way of informing a user of recent status changes, applicant believes that the use of high frequency auto-polling is inefficient and can cause a relatively high amount of power to be consumed. For example, under certain circumstances, there can be a relatively long time period where the status does not change. In such a case, high frequency auto-polling can cause power to be unnecessarily consumed and would be an inefficient use of first microprocessor 228. The following will describe a method to communicate the status of pump 300 in a timely manner while using a relatively low amount of power and microprocessing capability of remote controller 200.

In an embodiment for reducing power consumption, a method to communicate a status change of pump 300 can include interrogating pump 300 at a relatively low frequency such as, for example, about every 5 minutes. To asynchronously supplement the low frequency auto-polling process, pump 300 can be configured to add a status indicator with every wireless signal transmitted by pump 300. Pump 300 can send a wireless signal that includes a status indicator when microprocessor 228 detects a status change. In addition, pump 300 can also send a wireless signal that includes a status indicator when responding to a command from remote controller 200. For example, when a user initiates a command or query at remote controller 200, a wireless signal is sent to the pump 300, which in turn causes a responding wireless signal to be sent from pump 300 that includes a status indicator.

Examples of commands that can be sent to from remote controller include initiating a bolus or a home screen informational request. For the situation in which a user depresses a button for requesting home screen information, remote controller 200 sends a wireless query to pump 300. As a result, pump 300 can transmit a responding wireless signal, which includes data such as pump time, pump battery level, pump basal rate, and insulin remaining. In addition, the responding wireless signal can also includes a status indicator.

Each wireless signal 400 can include a plurality of bytes for communicating between pump 300 and remote controller 200. The first byte or header portion can contain a status indicator that is included in each wireless signal 400 sent by pump 300. In an embodiment, the first byte can contain three types of status indicators that are flagged at three discrete bit locations. Note that the use of only three types of status indicators is an exemplary embodiment and should not be construed as a limiting factor. One skilled in the art would appreciate that a different number of status indicators could be used as an embodiment. The three bit locations can be bits 4, 5, and 6 of the first byte. Bit 4 of the first byte can be used to set a flag for an error, alarm, or warning state. Bit 5 of the first byte can be used to set a flag for a reminder state. Bit 6 of the first byte can be used to set a flag for a busy state. In an embodiment, a wireless signal can have one bit flagged, two of the three bits flagged, or all of the three bits flagged. To efficiently use the bandwidth of microprocessor 228, a prioritization algorithm can be used to determine how remote controller 200 will respond to a particular flag or combination of flags.

The following will describe more details regarding the statuses associated with bits 4, 5, and 6. Bit 4 can be used to indicate a high priority status change. For example, the status change for bit 4 can include an error state, an alarm state, or a warning state. The error state can include more specific sub-states, which are associated with electronic errors such as, for example, a check sum error and a defective electrically erasable memory. The alarm state can include more specific sub-states, which are replace battery, replace insulin cartridge, and remove occlusion in the pump tubing or needle. The warning state, can include more specific sub-states, which are suspend pump activity, pump not primed, no cartridge is detected, insulin level too low in the cartridge, insulin amount exceeds total daily limit, insulin amount exceeds maximum bolus limit, wireless communication lost during remote bolus, insulin amount exceeds two hour limit, insulin amount exceeds maximum basal limit, basal pumping suspended, bolus canceled at pump, low battery, and low cartridge.

In an embodiment, bit 5 can be used to indicate a reminder state. For example, the reminder state change can include more specific sub-states, which are an alarm clock and a post-bolus reminder. The alarm clock can be a specific time programmed into pump 300 by a user so that a user can be alerted at a later time. The alarm clock can be a prompt, outputted on a screen of remote controller 200, to remind a user to perform a specific act such as, for example, to initiate a bolus of insulin. The post-bolus reminder can be set so that a reminder is triggered at either 1, 2, 3, or 4 hours after a bolus was delivered.

In an embodiment, bit 6 can be used to indicate a busy state. For example, the busy state can notify remote controller 200 that pump 300 is busy performing a time intensive operation such as, for example, a combination bolus. In the busy state, remote controller 200 can be restricted from performing a particular set of operations until the busy state is cleared.

Now that the three types of status indicators have been described, the following will describe the prioritization algorithm for processing changes in status. Once pump 300 detects a status change, pump 300 can send a first wireless signal 400, which includes the status indicator. Next, remote controller 200 can receive the status indicator. Using first microprocessor 228 of remote controller 200, the status indicator can be prioritized based on which bit is flagged or on which combination of bits are flagged. Depending on which bit or bits are flagged, remote controller 200 can immediately send a second wireless message to pump 300 to query for more information about the status, wait for an amount of time before sending a query, or do nothing.

In one scenario, remote controller 200 can receive a wireless signal that includes a flag on only bit 4. Remote controller 200 will then send a responding wireless signal to pump 300 to query for more information about the status change. Upon receipt of the responding wireless signal by pump 300, pump 300 will send specific information about the status change, which can include one of the three states (e.g., error, alarm, or warning state) and a sub-state. If there is an error state, remote controller 200 may prompt the user to re-set the power button on pump 300 to clear the flag on bit 4. If there is an alarm or warning state, remote controller 200 may prompt the user to acknowledge the alarm state by performing an input on the user interface. For a particular sub-state such as an occlusion, pump 300 can also suspend all activity such as basal pumping and/or sending an insulin bolus, in addition to requiring a user to acknowledge the alarm state by performing an input on the user interface.

Under certain circumstances, pump 300 can be in the process of delivering a bolus of insulin when an alarm is triggered at pump 300. For instance, an occlusion or low battery can be detected at pump 300 during the bolus. Even though pump 300 is performing the specific function of delivering a bolus, pump 300 can send a wireless signal that includes a flag on bit 4 of the status indicator. Remote controller 200 can then send a query to pump 300 to investigate the type of alarm, error, or warning that occurred on pump 300. The flag on bit 4 will remain set until the alarm, error, or warning condition has been resolved such as, for example, by removing the occlusion or replacing a low battery.

In another scenario, remote controller 200 can receive a wireless signal that includes a flag on only bit 5. Remote controller 200 will then send a responding wireless signal to pump 300 to query for more information about the status change. However, if remote controller 200 had received a wireless signal that included flags on both bit 4 and bit 5, remote controller 200 would first send a responding wireless signal to query for more information about the status change regarding bit 4. A responding wireless query for bit 5 will occur at a later time because bit 4 can be configured to have a higher priority than bit 5. Once remote controller 200 sends a responding wireless query for bit 5, pump 300 will send specific information about the status change such as, for example, an alarm clock reminder or a post-bolus reminder 1, 2, 3, or 4 hours after the bolus. Next, a user will be prompted to acknowledge the reminder state by performing an input on the user interface of remote controller 200.

In an embodiment, some commands of pump 300 will have a low priority such as, for example, transmitting glucose concentration values from remote controller 200 to pump 300. After performing a measurement at remote controller 200, the glucose concentration is saved to memory and transmitted to pump 300 when there is a time interval of low activity at remote controller 200. Transmitting glucose concentrations from remote controller 200 to pump 300 is a relatively low priority activity. If either bit 4 or bit 5 has a flag, then the glucose transmitting step will not occur. Under certain circumstances, a relatively large number of glucose measurements can be saved on the memory of remote controller 200 without having been transmitted to pump 300 because of a large amount of user activity with remote controller 200. However, once remote controller 200 is not in active use, all of the saved glucose measurement values will be sent to pump 300. If an alarm occurs during the transmission of a plurality of glucose measurements, the transmission will stop so that remote controller can investigate the alarm.

In another scenario, remote controller 200 can receive a wireless signal that includes a flag on bit 6, which indicates that a combo bolus is in progress. As a result, remote controller 200 will restrict pump 300 from performing specific set of functions until the combo bolus is completed. It should be noted that unlike flags on bit 4 and bit 5, remote controller does not send a responding query for a flag on bit 6. Examples of the specific set of functions that can be restricted include an additional combo boluses or an additional two-part combo bolus. In addition, remote controller 200 will output the status of the combo bolus on first display 202. Once pump 300 finishes the combo bolus, a wireless signal can be sent to clear the flag on bit 6.

In another scenario, remote controller 200 can receive a wireless signal that includes a combination of flags that include bit 6. An example of such a combination could be bits 4, 5, and 6; 4 and 6; and 5 and 6. Because a flag on bit 6 does not require a responding query, remote controller 200 will then send a responding query to a flag on bit 4 and/or bit 5 as described above.

What is claimed is:

1. A drug infusion system, comprising:
    a drug infusion device having a first microprocessor for creating, sending and receiving packets of data;
    a control unit comprising a second microprocessor for, at least, receiving the packets of data and determining the content of the packet of data; and
    a display screen visible to a user of the control device,
    wherein the first microprocessor is configured to create packets of data comprising a header byte having multiple bits wherein each bit of the header byte comprises a flag specific to only one of at least three states of the drug infusion device, and the second microprocessor is configured to generate a screen display to communicate the state of the drug infusion device to the user of the control device.

2. The drug infusion system of claim 1, wherein the header byte comprises at least three bits, each bit of the three bits being specific to only one state of the drug infusion device.

3. The drug infusion system of claim 2, wherein the at least three states of the drug infusion device comprises an error, an alarm, a warning, a reminder, or a busy state.

4. The drug infusion system of claim 1, wherein the packets of data including the header byte are transmitted from the drug infusion device to the control unit via wireless, radio-frequency transmission and the at least three bits comprise respectively bit 4, bit 5 and bit 6 of the header byte.

* * * * *